United States Patent [19]

Broersma, Jr. et al.

[11] 4,343,808
[45] Aug. 10, 1982

[54] METHOD OF INHIBITING SICKLING OF SICKLE ERYTHROCYTES

[75] Inventors: Robert J. Broersma, Jr., Noblesville, Ind.; Gayle A. Spittka, Midland, Mich.

[73] Assignee: The Dow Chemical Company, Midland, Mich.

[21] Appl. No.: 200,245

[22] Filed: Oct. 24, 1980

Related U.S. Application Data

[63] Continuation-in-part of Ser. No. 88,427, Oct. 25, 1979, abandoned.

[51] Int. Cl.³ .......................................... A61K 31/415
[52] U.S. Cl. ................................................ 424/273 R
[58] Field of Search ..................................... 424/273 R

[56] References Cited
PUBLICATIONS

Raper *Ann. Soc. Belle Med. Trop.* 1969, 49, 2, 205–210.

*Primary Examiner*—Frederick E. Waddell

[57] ABSTRACT

Method for inhibiting the sickling of sickle erythrocytes in blood by contacting the sickle erythrocytes with a compound of the formula:

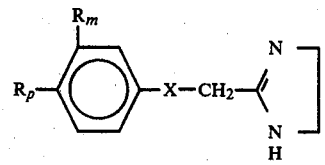

or a pharmaceutically-acceptable salt thereof wherein X represents sulfur, oxygen or imino; and $R_m$ and $R_p$ each independently represent hydrogen, cyano, nitro, alkylthio, alkylsulfinyl, alkylsulfonyl, alkyl or trifluoromethyl.

9 Claims, No Drawings

METHOD OF INHIBITING SICKLING OF SICKLE ERYTHROCYTES

CROSS-REFERENCE TO RELATED APPLICATION

This is a continuation-in-part of Ser. No. 088,427 filed Oct. 25, 1979, abandoned.

BACKGROUND OF THE INVENTION

In the adult human most hemoglobin is hemoglobin A (Hb-A) consisting of two alpha and two beta polypeptide chains. Certain individuals have an abnormal hemoglobin known as hemoglobin S (Hb-S) which results from the hereditary substitution of valine for glutamic acid in the sixth amino acid position in the beta polypeptide chains of hemoglobin. The proportion of Hb-S to Hb-A in such an individual depends upon whether the individual is a homozygous or heterozygous individual. The tendency toward sickling, that is, the formation of abnormally shaped erythrocytes in which the erythrocytes assume a sickle shape, depends upon the amount of Hb-S in the erythrocyte and the level of oxygen tension. Erythrocytes with 100 percent Hb-S sickle at physiological oxygen tensions, however as the amount of Hb-A increases and Hb-S decreases progressively lower oxygen tensions are required to induce sickling. The homozygous individual has 80 to 100 percent of the hemoglobin in the Hb-S form and sickling occurs at ordinary oxygen tensions. Such individuals are said to have sickle cell disease. Heterozygous individuals are said to possess sickle cell trait since only 25 to 40 percent of their hemoglobin is Hb-S, and sickling occurs only at unusually low oxygen tensions.

The presence of sickled erythrocytes can have severe implications since sickled erythrocytes encounter mechanical difficulties in moving through small vessels and the consequent stasis and jamming of these cells can lead to thrombosis and tissue anoxia. In addition, because of the sickled erythrocytes' increased mechanical fragility, hemolysis results, S. L. Robbins and M. Angell, "Basic Pathology", W. B. Saunders Company, Philadelphia, London, Toronto, 1971, pp. 127 and 282.

A treatment or test in which the sickling of red blood cells prone to sickle (sickle erythrocytes) is inhibited or reversed would be useful in the treatment of afflicted individuals or for the study of the sickling phenomenon.

SUMMARY OF THE INVENTION

It has now been discovered that the sickling in blood of red blood cells prone to sickle can be inhibited by contacting the sickle erythrocytes in blood with an effective amount of a compound of the formula:

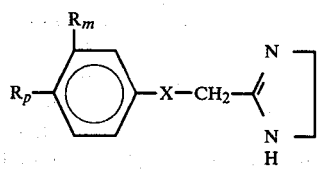

(I)

or a pharmaceutically-acceptable salt thereof wherein X represents sulfur, oxygen or imino (—NH—); and $R_m$ and $R_p$ each independently represent hydrogen, cyano, nitro, alkylthio, alkylsulfinyl, alkylsulfonyl, alkyl or trifluoromethyl.

As used herein, the term "alkyl" refers to an alkyl group of from 1 to 3 carbon atoms such as methyl, ethyl, propyl and isopropyl; those substituents which incorporate the term "alkyl" refer to groups in which the alkyl portion has from 1 to 3 carbon atoms, thus, for example, "alkylsulfonyl" refers to methylsulfonyl, ethylsulfonyl, propylsulfonyl and isopropylsulfonyl.

"Pharmaceutically-acceptable salt" refers to non-toxic acid addition salts of the compounds, the anions of which are relatively innocuous to mammals at exposure levels or dosages consistent with activity or use of the compounds, so that the beneficial effects of the free base are not vitiated by the side effects, or mammalian toxicity, ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids.

As used herein, an effective amount of the compound represented by formula I or a pharmaceutically-acceptable salt thereof is that amount of the compound or its pharmaceutically-acceptable salt which when employed according to the method of the present invention is sufficient to inhibit the sickling of sickle erythrocytes in blood. As used in the specification and claims, "inhibiting" means inhibiting the formation of sickle morphology and also includes actively reversing sickled cells to a more normal or typical morphology, in cases in which sickling has already occurred. The compounds used in the practice of the present invention are therefore particularly useful in the study of the sickling phenomenon, in the investigation of the effects of chemical substances on erythrocytes and has potential usefulness as a treatment for individuals subject to the sickling phenomenon.

DETAILED DESCRIPTION OF THE INVENTION

The compounds used in the practice of the present invention, i.e., the compounds of formula I or a pharmaceutically-acceptable salt thereof, are prepared by reacting the appropriate substituted-phenoxyacetonitrile, substituted-phenylthioacetonitrile or substituted-anilinoacetonitrile represented by the formula:

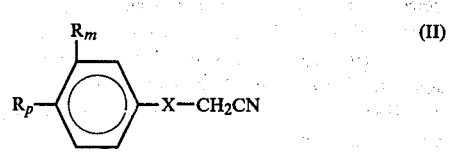

(II)

wherein X, $R_m$ and $R_p$ are defined as for formula I, with ethylenediamine p-toluenesulfonate. The reaction is conveniently accomplished employing a procedure similar to that used for the preparation of 2-((halophenoxy)methyl)-2-imidazolines, as described in U.S. Pat. No. 3,449,356. In preparing the 2-imidazoline compounds of formula I, the appropriate acetonitrile, i.e., formula II compound, and the ethylenediamine p-toluenesulfonate are mixed and heated together in an inert organic solvent, such as 1,2-dichlorobenzene for a time sufficient to obtain the desired 2-imidazoline p-toluenesulfonate salt. The reaction is preferably carried out under an inert atmosphere, accomplished by passing nitrogen through the reaction mixture to carry off the ammonia formed during the reaction.

The 2-imidazoline p-toluenesulfonate salt can be separated from the reaction mixture using known procedures such as adjustment of reaction mixture concentration, filtration, centrifugation or decantation. The 2-imidazoline p-toluenesulfonate salt can be purified by conventional procedures such as recrystallization and washing.

Alternatively, the 2-imidazoline p-toluenesulfonate salt can be converted to the free base form (i.e., free imidazoline) by hydrolysis in aqueous base. The free base is then separated by extraction with an organic solvent such as methylene chloride ($CH_2Cl_2$) or chloroform ($CHCl_3$), followed by evaporation of the solvent. Purification of the free base is accomplished by conventional methods such as recrystallization or the free base can be converted to a pharmaceutically-acceptable salt by treating the free base with the appropriate organic or mineral acid. The pharmaceutically-acceptable salt can be purified by known procedures such as recrystallization.

Those compounds of formula I in which $R_m$ or $R_p$ are alkylsulfinyl or alkylsulfonyl can also be readily prepared by oxidizing the appropriate formula I compound in which $R_m$ or $R_p$ is alkylthio. Considerations such as the reactivity of the starting compound can dictate the choice of the most appropriate oxidizing agent and conditions to be employed for the oxidation reaction.

The substituted-phenoxyacetonitrile, substituted-phenylthioacetonitrile or substituted-anilinoacetonitrile reactants, illustrated by formula II, are prepared by known procedures, for example, by reacting a substituted-(phenol or phenylthiol or aniline) of the formula:

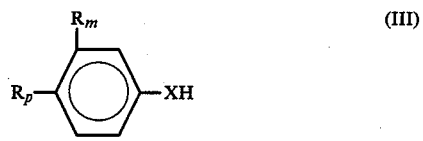

(III)

wherein X, $R_m$ and $R_p$ are as defined for formula I, and chloroacetonitrile. The reaction is accomplished by heating the reactants, usually in the presence of a base such as potassium carbonate ($K_2CO_3$) and an inert organic solvent such as dimethylformamide (DMF) or dimethyl sulfoxide (DMSO), for a time sufficient to obtain the desired acetonitrile. Especially in cases where X is —NH—, it may be desirable to simply heat the appropriate formula III compound and chloroacetonitrile neat. The acetonitrile is recovered and purified by conventional procedures such as those described herein.

The following examples are included to further illustrate the invention but are not to be construed as a limitation thereon.

EXAMPLE 1

2-(3-Nitrophenoxy)methyl)-2-imidazoline p-Toluenesulfonate (a) Preparation of 3-nitrophenoxyacetonitrile A mixture of 41.7 grams (g) of 3-nitrophenol, 24 g of chloroacetonitrile and 58.8 g of anhydrous $K_2CO_3$ in 60 milliliters (ml) of DMSO was heated with stirring in a round-bottomed three-necked flask at 70°–80° C. for 3 hours. The reaction mixture was then poured into 1200 ml of ice and water, which resulted in crystal formation. When all of the ice had melted, the solids were filtered, washed well with water and dried overnight in a vacuum oven. The solids were then put in solution in 400 ml of boiling absolute ethanol, treated with activated charcoal and then filtered. The filtrate was cooled to 0° C. and the resulting solids removed by filtration. Drying in a vacuum oven gave 47 g of 3-nitrophenoxyacetonitrile as a pale tan solid having a melting point (m.p.) of 93°–95° C.

(b) Preparation of 2-(3-nitrophenoxy)methyl)-2-imidazoline p-toluenesulfonate

A mixture of 26.7 g of 3-nitrophenoxyacetonitrile and 35.0 g of ethylenediamine p-toluenesulfonate in 100 ml of 1,2-dichlorobenzene was stirred in a round-bottomed three-necked flask at 128° C.–137° C. for about 1½ hours under a small flow of nitrogen, essentially as described in U.S. Pat. No. 3,449,356. The reaction mixture was cooled, resulting in crystal formation. Methylene chloride was added to the reaction mixture and then the mixture was filtered to obtain the crude product. The crude product was washed with $CH_2Cl_2$ and then put in solution in approximately 400 ml of boiling absolute ethanol, treated with activated charcoal and filtered. The filtrate was cooled and then filtered to obtain 53 g of purified 2-((3-nitrophenoxy)methyl-2-imidazoline p-toluenesulfonate as pale tan crystals, m.p. 165°–167° C.

EXAMPLE 2

2-((4-Cyanophenoxy)methyl)-2-imidazoline p-Toluenesulfonate (a) Preparation of 4-cyanophenoxyacetonitrile The compound of 4-cyanophenoxyacetonitrile was prepared by heating 29.8 g of 4-cyanophenol, 44.8 g of anhydrous $K_2CO_3$, 40 ml of dimethylformamide and 18.75 g of chloroacetonitrile with stirring in a round-bottomed three-necked flask at 70°–80° C. for 3 hours, after which time the reaction mixture was poured into an ice and water mixture, which resulted in crystal formation. The crystals were separated by filtering and were then washed with water. After drying a pale tan solid was obtained which was then dissolved in methylchloroform at reflux temperature, treated with activated charcoal and filtered. The filtrate was cooled to 5° C. and the resulting crystals filtered and dried to give the 4-cyanophenoxyacetonitrile.

(b) Preparation of 2-((4-cyanophenoxy)methyl)-2-imidazoline p-toluenesulfonate

A mixture of 15.8 g of 4-cyanophenoxyacetonitrile and 23.3 g of ethylenediamine p-toluenesulfonate in 50 ml of 1,2-dichlorobenzene was heated at from about 130°–145° C. for about an hour. After reaction the mixture was cooled, diluted with $CH_2Cl_2$ and filtered to obtain the crude product. The crude product was dissolved in boiling absolute ethanol, treated with activated charcoal and filtered through a fluted paper. The filtrate was cooled to 5° C. for 1.5 hours and the crystals which formed removed by filtering. After drying in a vacuum oven, off-white crystals were obtained having a melting point of 190°–192° C. The off-white crystals were put in solution in 200 ml of boiling water and treated with activated charcoal and filtered. The filtrate was cooled to 5° C. for 1 hour and the crystals which formed removed by filtration. Upon drying, the product 2-((4-cyanophenoxy)methyl)-2-imidazoline p-toluenesulfonate was obtained as white crystals, m.p. 196°–198° C.

EXAMPLE 3

2-((4-(Methylsulfonyl)phenoxy)methyl)-2-imidazoline Hydrochloride (a) Preparation of 4-methylthiophenoxyacetonitrile The compound 4-methylthiophenoxyacetonitrile was prepared by heating 4-methylthiophenol, chloroacetonitrile and anhydrous $K_2CO_3$ in DMSO, employing substantially the same procedure described in previous examples.

(b) Preparation of 2-((4-(methylthio)phenoxy)methyl)-2-imidazoline hydrochloride A mixture of 27 g of 4-methylthiophenoxyacetonitrile and 35 g of ethylenediamine p-toluenesulfonate in 50 ml of 1,2-dichlorobenzene was heated at 158°–180° C. for about 45 minutes. The reaction mixture was cooled, diluted with $CH_2Cl_2$ and filtered to obtain the p-toluenesulfonate salt. After washing with $CH_2Cl_2$, the p-toluenesulfonate salt was slurried with water and then 40 ml of an aqueous 5 normal (N) sodium hydroxide solution added to the slurry. Extracting the mixture with $CH_2Cl_2$ and then evaporating the $CH_2Cl_2$ left 30 g of the free base. The free base was heated in cyclohexane/methylchloroform, the resulting mixture was then cooled and the solids removed by filtration. The free base was then dissolved in 150 ml of isopropanol and acidified with hydrochloric acid (HCl) in isopropanol to give the hydrochloride salt (31 g). The 2-((4-(methylthio)phenoxy)methyl)-2-imidazoline hydrochloride was found to have a m.p. of 190°–191° C.

(c) Preparation of 2-((4-(methylsulfonyl)phenoxy)methyl)-2-imidazoline hydrochloride A mixture of 10 g of 2-((4-(methylthio)phenoxy)methyl)-2-imidazoline hydrochloride, 100 ml of glacial acetic acid and 10 g of 30% hydrogen peroxide was warmed at from about 78°–105° C. for about 3 hours. The mixture was cooled and then poured into water. The solution was made alkaline and extracted with $CH_2Cl_2$. The $CH_2Cl_2$ was evaporated leaving 7 g of the free base. The free base was dissolved in isopropanol and acidified with HCl in isopropanol. After standing overnight, the mixture was filtered and 6.5 g of 2-((4-methylsulfonyl)phenoxy)methyl)-2-imidazoline hydrochloride recovered, m.p. 230° C. (decomposition).

EXAMPLE 4

2-(3-Cyanophenoxy)methyl)-2-imidazoline p-Toluenesulfonate (a) Preparation of 3-cyanophenoxyacetonitrile The compound 3-cyanophenoxyacetonitrile was prepared by heating 20.0 g of 3-cyanophenol, 30.1 g of anhydrous potassium carbonate and 30 ml of dimethylformamide with stirring in a 250 ml round-bottomed three-necked flask to 70° C. and then 12.7 g of chloroacetonitrile was added dropwise over a 15 minute period with cooling. The temperature of the mixture was held at 70°–80° C. for three hours, after which time the reaction mixture was poured into approximately 700 ml of ice and water which resulted in crystal formation. The crystals were separated by filtering and then washed thoroughly with water. After drying in a vacuum oven, a tan solid 3-cyanophenoxyacetonitrile was obtained.

(b) Preparation of 2-((3-cyanophenoxy)methyl)-2-imidazoline p-toluenesulfonate

A mixture of 12.64 g of 3-cyanophenoxyacetonitrile, 18.6 g of ethylenediamine p-toluenesulfonate and 35 ml of 1,2-dichlorobenzene was stirred and the reaction carried out substantially as described in Example 2 herein.

The reaction mixture was cooled and the solid formed was filtered and washed with $CH_2Cl_2$. Recrystallization was accomplished by dissolving the solid in 225 ml of absolute ethanol at reflux temperature. The solution was treated with activated charcoal and filtered while hot through a fluted paper. After cooling the solution for ½ hour at 5° C., the solution was filtered to obtain the product, 2-((3-cyanophenoxy)methyl)-2-imidazoline p-toluenesulfonate as white crystals which after drying in a vacuum oven had a melting point of 170°–172° C.

EXAMPLE 5

2-((4-(Methylthio)-m-tolyloxy)methyl)-2-imidazoline (a) Preparation of 4-methylthio-m-tolyloxyacetonitrile The compound 4-methylthio-m-tolyloxyacetonitrile was prepared substantially as described in previous examples by heating a mixture of 55.0 g of 4-methylthio-m-cresol, 30 g of chloroacetonitrile, 70.7 g of anhydrous $K_2CO_3$ and 104 ml of DMSO, which gave 66.0 g of the compound as a reddish oil.

(b) Preparation of 2-((4-(methylthio)-m-tolyloxy)methyl)-2-imidazoline

The product, 2-((4-(methylthio)-m-tolyloxy)methyl)-2-imidazoline, was prepared by heating 19.3 g of 4-methylthio-m-tolyloxyacetonitrile, 23.3 g of ethylenediamine p-toluenesulfonate and 75 ml of 1,2-dichlorobenzene substantially as described in previous examples. Upon cooling the reaction mixture, diluting with $CH_2Cl_2$ and filtering, 32.5 g of p-toluenesulfonate salt was obtained. The p-toluenesulfonate salt was then slurried in water and $CH_2Cl_2$ and then basified. The $CH_2Cl_2$ layer was separated and the aqueous layer extracted with chloroform. The extracts were combined, treated with diatomaceous earth and activated charcoal and then filtered. The filtrate was taken to dryness, which gave 13.5 g of the product, 2-((4-(methylthio)-m-tolyloxy)methyl)-2-imidazoline as a white solid, m.p. 102°–104° C.

EXAMPLE 6

2-((3-Trifluoromethylanilino)methyl)-2-imidazoline Hydrochloride (a) Preparation of m-trifluoromethylanilinoacetonitrile Chloroacetonitrile (16 g), m-aminobenzotrifluoride (32.2 g), $K_2CO_3$ (39.2 g) and DMSO (40 ml) were heated with stirring in a round-bottomed three-necked flask at 70°–80° C. for 4.0 hours. Pouring the reaction mixture into approximately 1 liter of ice and water resulted in the formation of an oil. The mixture was extracted with $CH_2Cl_2$ and the extracts obtained treated with diatomaceous earth and activated charcoal, and then filtered. The filtrate was taken to dryness, which gave 29.5 g of m-trifluoromethylanilinoacetonitrile as a dark oil.

(b) Preparation of
2-((3-trifluoromethylanilino)methyl-2-imidazoline hydrochloride A mixture of 29.5 g of m-trifluoromethylanilinoacetonitrile, 34.4 g of ethylenediamine p-toluenesulfonate in 70 ml of 1,2-dichlorobenzene was heated at 124°–168° C. for about 1½ hrs. The free imidazoline was recovered as an oil utilizing substantially the same procedures described previously herein. The free imidazoline was put in solution in isopropyl alcohol, treated with activated charcoal and then filtered. Acidification with HCl in isopropanol resulted in the formation of solids. The mixture was cooled and filtered and 8.1 g of 2-((3-trifluoromethylanilino)methyl)-2-imidazoline hydrochloride obtained, m.p. 218°–220° C.

Other compounds prepared utilizing substantially the same procedures as those described herein, are:

EXAMPLE 7

2-(3-Trifluoromethylphenoxy)methyl-2-imidazoline Hydrochloride, m.p. 231°–233° C.

EXAMPLE 8

2-(Phenoxymethyl)-2-imidazoline Hydrochloride, m.p. 170.5°–171.5° C.

In practicing the method of the invention, the imidazoline compounds are brought into contact with sickle erythrocytes, typically by introducing an effective amount of the compound into the blood of a mammal having blood containing erythrocytes subject to sickling. Introducing an effective sickle inhibiting amount of the above-noted compound or pharmaceutically-acceptable salt into the blood of such a mammal can be carried out directly, e.g., by direct addition to blood samples, or indirectly, by administering the compound to the mammal in a manner effective to provide the sickle inhibiting concentration in the blood stream.

The compound or pharmaceutically-acceptable salt thereof would be introduced using a route of administration which provides an effective but non-toxic concentration of the compound in the blood, either by oral ingestion or direct administration as, for example, intravenous infusion or injection. The amount to be administered would vary depending on the compound or pharmaceutically-acceptable salt employed, the type of erythrocyte sickling inhibition or reversal desired, the size and nature of the mammal, and the manner of contacting the blood. When used to inhibit erythrocyte sickling in a mammal, the quantity of compound or pharmaceutically-acceptable salt to be administered in particular instances can be determined by routine procedures, such as studies of the concentration of the compound in the blood obtained at various time intervals after administration, using various methods of administration, and in vitro studies of the anti-sickling effect obtained with various concentrations of the compound in the particular blood in question.

The compound 2-((4-cyanophenoxy)methyl)-2-imidazoline p-toluenesulfonate (Example 2) and 2-((3-cyanophenoxy)methyl)-2-imidazoline p-toluenesulfonate (Example 4) were tested for anti-sickling activity using a suspension of intact sickle cells as follows:

Blood collected from individuals with homozygous sickle cell disease, as well as normal blood, was anticoagulated with ethylenediaminetetraacetic acid (EDTA) and refrigerated until used. To portions of the blood samples were added appropriate volumes of a solution of the compound to be tested so that final concentrations of 0.0125 molar (M), 0.025 M, 0.05 M or 0.1 M were obtained, and the mixtures were incubated at 37° C. for 30 minutes. The test compounds were dissolved in saline. Appropriate volumes of saline were added to the control samples. Urea in invert sugar (UIS) at 0.05 M to 1.5 M concentrations was used as an agent capable of transforming sickled cells into normal forms and was therefore used as a positive control.

Sickling was induced chemically by reducing the blood samples with an equal volume of a 2% solution of sodium metabisulfite in phosphate-buffered saline for 30 minutes.

Anoxic sickling (deoxygenation) was induced by exposing sickle blood to a hydrated 95% nitrogen, 5% carbon dioxide atmosphere for 60 minutes.

After the sickling stimulus, slides were prepared. A volume of 0.2 ml of sickled cells were fixed in 1.0 ml of 3.2% glutaraldehyde in 0.1 M cacodylic buffer. Wet slides were prepared and sealed.

The slides were scored for normal cells (Typ.), atypical cells (Atyp.) and sickled cells (Sickle) on the basis of counting 300 cells per slide. The compound of Example 2 was tested in both the deoxygenation induced and chemically induced sickling systems and the compound of Example 4 was tested in the deoxygenation induced sickling system. The results of this "Blockade Erythrocyte Morphology" are presented in Table 1.

TABLE 1

| Compound Example Number | M | BLOCKADE ERYTHROCYTE MORPHOLOGY Percent Change | | | | | | | | |
|---|---|---|---|---|---|---|---|---|---|---|
| | | Deoxygenation | | | | | Chemically Induced | | | |
| | | n | Typ. | Atyp. | Sickle | Lysis | n | Typ. | Atyp. | Sickle | Lysis |
| 2 | 0.025 | 5 | +86 | −36 | −19 | — | 1 | +56 | −14 | −27 | — |
| | 0.05 | 5 | +106 | −36 | −27 | — | 2 | +84 | +138 | −29 | — |
| | 0.1 | 5 | +170 | −39 | −61 | ± | 1 | +78 | −63 | −32 | ± |
| 4 | 0.0125 | 1 | +201 | −65 | −33 | — | | | | | |
| | 0.025 | 1 | +316 | −78 | −69 | — | | | | | |
| | 0.05 | 2 | +407 | −74 | −77 | — | | | | | |

Table 1 shows that both the compounds of Example 2 and Example 4 interfered with deoxygenation induced sickling and both compounds exhibited this activity at a 0.05 M concentration without the appearance of cell lysis (in both Tables 1 and 2 a negative number indicates the percent reduction in the denoted cell type as compared to a control, whereas a positive number indicates a percent increase in the denoted cell type as compared to the control, the symbol ± in the "Lysis" column indicates the appearance of some cell lysis at that particular test compound concentration, "M" represents the molar concentration of the test compound in the sample tested and "n" indicates the number of test runs). The compound of Example 2 showed a slightly sickling inhibitory effect in the chemically induced sickling test system.

The compound 2-((4-cyanophenoxy)methyl)-2-imidazoline p-toluenesulfonate (Example 2) was tested for its ability to reverse the sickling process by first applying the hereinabove noted sickling stimuli to the sickle cell blood and then adding the test compound to the red cell suspensions. Results of this "Reverse Erythrocyte Morphology" testing are presented in Table 2.

TABLE 2

| Compound Example Number | M | n | REVERSE ERYTHROCYTE MORPHOLOGY Percent Change | | | | | | | |
|---|---|---|---|---|---|---|---|---|---|---|
| | | | Deoxygenation | | | | Chemically Induced | | | |
| | | | Typ. | Atyp. | Sickle | Lysis | n | Typ. | Atyp. | Sickle | Lysis |
| 2 | 0.025 | 1 | +133 | −22 | −47 | − | 1 | +48 | −49 | −27 | − |
| | 0.05 | 1 | +142 | −26 | −46 | − | 1 | +87 | −73 | −52 | ± |
| | 0.1 | 1 | +202 | −46 | −41 | ± | 1 | +86 | −96 | −48 | ± |

Table 2 indicates that 2-((4-cyanophenoxy)methyl-2-imidazoline p-toluenesulfonate effectively reversed sickling induced chemically or by deoxygenation over the ranges tested. There was some hemolysis observed in the chemically induced system at a 0.05 M concentration and some hemolysis observed in both systems at a 0.1 M test compound concentration.

The compounds described herein were tested in an "Oxygen-Affinity Assay" to measure the ability of the compound to influence the Hb-S oxygen affinity. There is a relationship between oxygen binding and Hb-S gelation and thus a measure of oxygen affinity is an index of Hb-S aggregation within the red blood cell. Hemoglobin S polymers decrease the overall oxygen affinity. Thus a return to normal of Hb-S oxygen affinity is a measure of decreased gelation.

For measurements of oxygen equilibria whole Hb-S blood was equilibrated in a tonometer at 37° C. and measurements were made in the presence of a 10 millimolar (mM) concentration of the test compound. Some of the compounds were also tested at a 5 mM concentration. The whole blood pH, oxygen tension, and blood $PO_2$ were measured.

The percentage of oxygen saturation was plotted against the partial pressure of oxygen (mm Hg). The $P_{50}$ value (oxygen tension at 50% saturation) was determined for each control and treated whole blood sample and the difference ($\Delta P_{50}$) between the control and treated whole blood sample noted. As used herein, a negative $\Delta P_{50}$ represents a change toward a normal Hb-S oxygen affinity and thus is a measure of the test compound's ability to inhibit the sickling of sickle erythrocytes. The results of the Oxygen-Affinity Assays are presented in Table 3.

TABLE 3

| Compound Example Number | Oxygen-Affinity Assay $\Delta P_{50}$ | |
|---|---|---|
| | 10 mM | 5 mM |
| 1 | −10.6 | −2 |
| 2 | −9.1 | |
| 3 | −7.0 | |
| 4 | −13.7 | −1 |
| 5 | −14.7 | −11 |
| 6 | −4.3 | |
| 7 | −3.0 | |
| 8 | −5.0 | |

The data in Table 3 shows that all of the test compounds at a 10 mM concentration exhibited a negative $\Delta P_{50}$ which indicates that the test compound inhibited the sickling of sickle erythroctyes. Several of the test compounds also inhibited the sickling of sickle erythrocytes at a 5 mM concentration.

The compound 2-((3-cyanophenoxy)methyl)-2-imidazoline p-toluenesulfonate was tested to determine its ability to inhibit sickle erythrocyte hemoglobin gelation as follows:

The solubility of deoxyhemoglobin S (Deoxy Hb-S) was determined utilizing substantially the same procedure described by Behe, M. J., Englander, S. W., *Biochemistry* 18: 4196–4201 (1979). Assays were done to determine the equilibrium solubility of Hb-S in the presence of inhibitor (i.e., test compound). To a concentrated solution of Hb-S in 0.1 molar phosphate, at pH 6.86, was added 0.75 M dithionite and a sufficient quantity of a 0.01 M solution of the test compound at pH 6.89 so that the resulting mixture had a 10 millimolar concentration of the test compound and a pH of 6.89. Test mixtures were placed in a 4 centimeter (cm) length of thin quartz tubing sealed at one end, and then incubated at 37° C. for two hours to achieve gelation, and then re-equilibrated in a water bath (20° C.) for 20 minutes. The quartz tubing containing the test mixture was then placed in a glycerol filled centrifuge tube (topped by a rubber ring to center the quartz tubing) and centrifuged for two hours at 140,000 times gravity. After centrifugation, the quartz tubing was broken above the pelleted gel and the supernatant hemoglobin removed. The concentration of the hemoglobin in the supernatant was determined by measuring the absorbance at 540 nanometers (nm) after a 300-fold dilution with normally oxygenated buffer.

The Relative Solubility is a measure of the ability of the test compound to increase the solubility of deoxyhemoglobin S and is readily determined by comparing the solubility of the treated (i.e., test compound present) sample versus the control (i.e., test compound absent) sample. A Relative Solubility value greater than 1.0 indicates that the deoxyhemoglobin S solubility was greater in the presence of test compound and demonstrates that the test compound was effective in inhibiting sickle erythrocyte hemoglobin gelation. The results of the deoxyhemoglobin S solubility testing are presented in Table 4.

TABLE 4

| Compound Example Number | Solubility of Deoxy Hb-S | | Relative Solubility (gm/dL treated) (gm/dL control) |
|---|---|---|---|
| | gm/dL* | | |
| | Control | Treated | |
| 4 | 17.4 | 19.2 | 1.10 |

*Solubility of deoxyhemoglobin S in grams/deciliter

The data in Table 4 indicates that the solubility of deoxyhemoglobin S was increased in the presence of a 10 mM concentration of 2-((3-cyanophenoxy)methyl)-2-imidazoline p-toluenesulfonate, which demonstrates the effectiveness of the compound in inhibiting sickle erythrocyte hemoglobin gelation.

Although the toxicity of individual compounds can vary, it has been found that some of the compounds are relatively non-toxic to mammals. For example, the compound of Example 2 has an $LD_{50}$ of 316 milligrams/kilogram of body weight in mice, when administered by intraperitoneal injection.

What is claimed is:

1. A method for inhibiting the sickling of red blood cells prone to sickle in blood containing said cells which comprises introducing into said blood an effective sickle inhibiting amount of a compound of the formula:

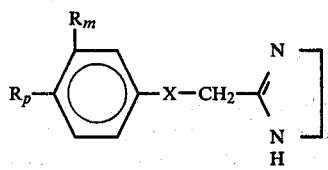

or a pharmaceutically-acceptable salt thereof wherein X represents sulfur, oxygen or imino; and $R_m$ and $R_p$ each independently represent hydrogen, cyano, nitro, alkylthio, alkylsulfinyl, alkylsulfonyl, alkyl or trifluoromethyl.

2. The method of claim 1 wherein the compound is 2-((3-nitrophenoxy)methyl)-2-imidazoline or a pharmaceutically-acceptable salt thereof.

3. The method of claim 1 wherein the compound is 2-((4-cyanophenoxy)methyl)-2-imidazoline or a pharmaceutically-acceptable salt thereof.

4. The method of claim 1 wherein the compound is 2-((4-(methylsulfonyl)phenoxy)methyl-2-imidazoline or a pharmaceutically-acceptable salt thereof.

5. The method of claim 1 wherein the compound is 2-((3-cyanophenoxy)methyl)-2-imidazoline or a pharmaceutically-acceptable salt thereof.

6. The method of claim 1 wherein the compound is 2-((4-(methylthio)-m-tolyloxy)methyl)-2-imidazoline or a pharmaceutically-acceptable salt thereof.

7. The method of claim 1 wherein the compound is 2-((3-trifluoromethylanilino)methyl)-2-imidazoline or a pharmaceutically-acceptable salt thereof.

8. The method of claim 1 wherein the compound is 2-((3-trifluoromethylphenoxy)methyl)-2-imidazoline or a pharmaceutically-acceptable salt thereof.

9. The method of claim 1 wherein the compound is 2-(phenoxymethyl)-2-imidazoline or a pharmaceutically-acceptable salt thereof.

* * * * *